Oct. 11, 1949. C. G. DUEHRSEN Plant Pat. 879
FLORIBUNDA ROSE PLANT
Filed Dec. 30, 1947
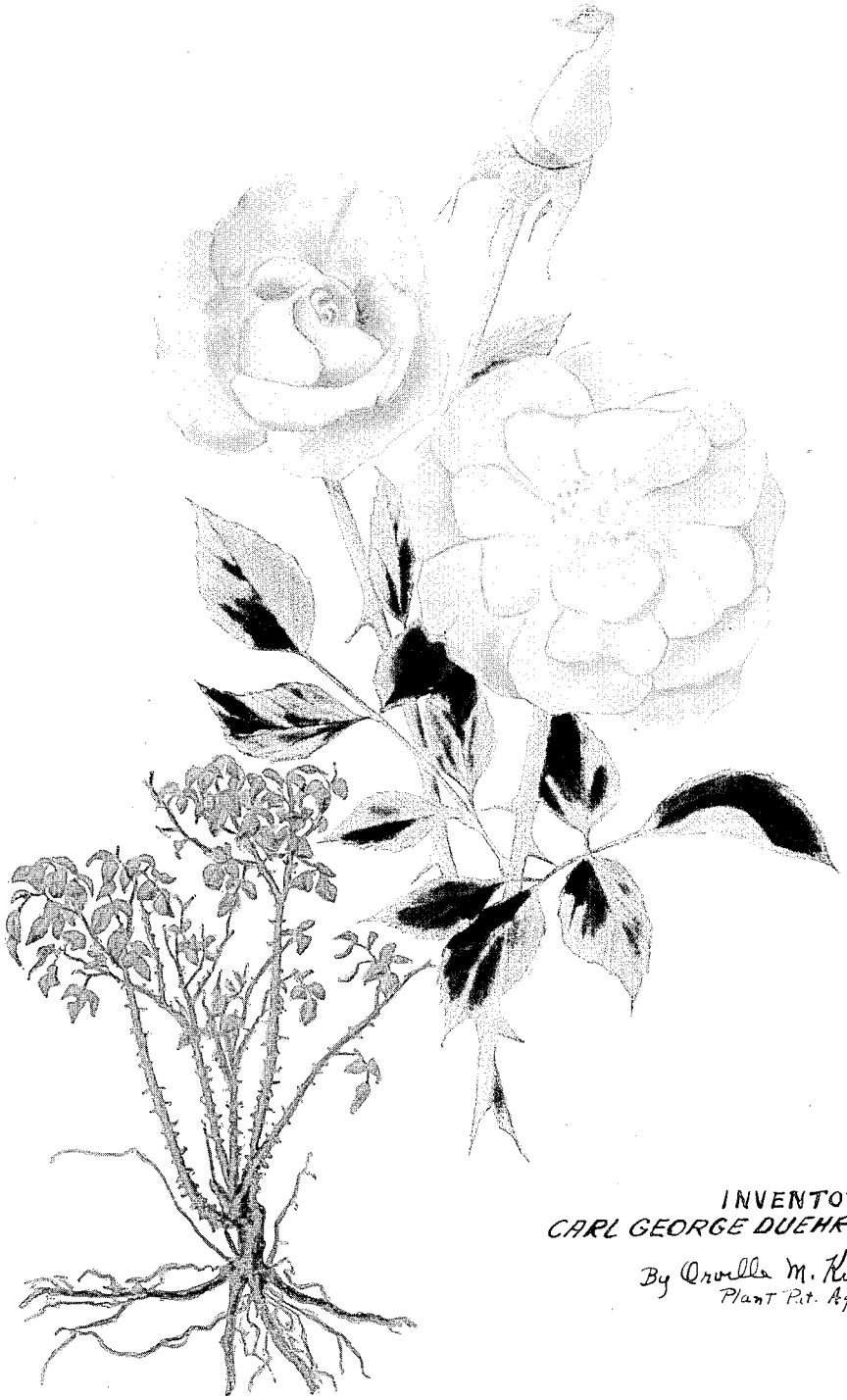
INVENTOR
CARL GEORGE DUEHRSEN
By Orville M. Kile
Plant Pat. Agt.

Patented Oct. 11, 1949

Plant Pat. 879

UNITED STATES PATENT OFFICE

879

FLORIBUNDA ROSE PLANT

Carl George Duehrsen, Montebello, Calif., assignor to Howard & Smith, Montebello, Calif.

Application December 30, 1947, Serial No. 794,765

1 Claim. (Cl. 47—61)

My present invention relates to an improved variety of rose plant of the floribunda novelty type. It is the result of a cross between Betty Uprichard and Heidekind but is very unlike either parent.

The plant manifests exceptional vigor and health and produces large quantities of attractive flowers the entire season. The flowers have a novel color for this type of rose and are borne in large even trusses. Because of the plant's abundant foliage and brilliant flower, it is particularly good for mass plantings such as hedges along driveways.

This new variety has been asexually reproduced from cuttings in the greenhouses of Howard & Smith at Montebello, California, and its characteristics appear to be permanent.

The accompanying illustration shows three typical specimens of the flower of my new variety in various stages of development and in approximately their true colors. Also a small sketch indicating plant form.

Following is a detailed description of the plant and flower of my new variety. Color plate numbers refer to Ridgway's Color Standards and Nomenclature. Where no number is given, the ordinary dictionary meaning is intended.

*The plant*

Form: Well-foliaged bush.

Growth: Plant has exceptional vigor. Attains a height of 3 feet in a given season, from fall-budded plants. Makes basal shoots in constant succession.

Disease resistance: Resistant to mildew and free from blackspot where it has been grown in southern California.

Blooming habit: Absolutely remontant throughout the entire season. Flowers are borne in large trusses of even umbrella-like contour and the bush is always a mass of color.

Stems:

*Color.*—Light green with reddish tinge.

*Strength.*—Very strong.

*Rigidity.*—Upright and rigid.

*Surface aspect.*—Smooth except for large thorns.

*Thorns.*—Numerous, large, scattered, reddish, slightly downward-pointing, and approximately ⅜ inch in length.

Foliage: Number of leaflets 5 to 7.

*Quantity.*—Well foliaged right down to the ground.

*Shape.*—Leaflets oval with acute base and acuminate apex. Serrations shallow.

*Size.*—Entire leaf approximately 4½ inches long.

*Texture.*—Very leathery.

*Color.*—Dull dark green.

*Leaf stem.*—Slender; long between leaflets; dull green with pinkish tinge.

*Stipules.*—Very narrow and short.

*The flower*

Bud:

*Size.*—About 1 inch long.

*Shape.*—Long and pointed.

*Color.*—In popular terms, color is rich coral salmon. Lies between Rose Doree (Plate I) and Spectrum Red (Plate I).

*Calyx and sepals.*—Simple; smooth-edged; reflex early.

*Peduncle.*—Very strong and rigid; short; red-tinged; has many large thorns.

Bloom:

*Borne.*—In very large trusses of even umbrella-like contour.

*Size.*—Individual flower is approximately 3 inches in diameter.

*Form.*—Loose and high-centered at first, opening into flat formal arrangement disclosing many stamens.

*Color.*—Approximately same as bud except that the center of the wide-open flower is slightly lighter in tone.

*Discoloration.*—None.

*Petalage.*—Semi-double, with 15 to 17 petals.

*Fragrance.*—Quite fragrant.

*Longevity.*—Lasts very well both on plant and as cut flower.

Petals:

*Shape.*—Obovate.

*Aspect.*—Very silky.

*Size.*—1½ inches from tip to base.

*Color.*—Almost uniformly deep rich salmon-pink, although slightly lighter at base.

*Arrangement.*—Imbricated and loose, with inner petals much shorter than outer ones which emphasizes the formal arrangement. Petals reflex only slightly at edges.

*Persistence.*—Petals cling very persistently in all types of weather.

Reproductive organs:

*Pistils.*—Few. Stigmas dull white. Styles short.

*Stamens.*—Many, surrounding pistils. Visible in open flower. Filaments rather short and reddish-tinged. Anthers large, dark yellow, and prominent in open flower. Pollen yellow.

*Fruit.*—Variety apparently sterile.

Having thus disclosed my invention, I claim:

The new and distinct variety of floribunda rose plant, substantially as herein shown and described, characterized particularly by its exceptional vigor of growth; its disease resistance; its abundant foliage; its absolutely remontant blooming habit; its large umbrella-like flower trusses; its long-pointed bud; and its fragrant flowers of novel rich coral salmon color.

CARL GEORGE DUEHRSEN.

No references cited.